(12) United States Patent
Kilps et al.

(10) Patent No.: US 7,631,568 B2
(45) Date of Patent: Dec. 15, 2009

(54) PARTICULATE MONITOR

(75) Inventors: Patrick James Kilps, Hubertus, WI (US); Michael Gene Wurm, Waukesha, WI (US); Thomas Edward King, Chicago, IL (US); Paul Ezekial James, Marietta, GA (US); Steven E. Michalski, Menomonee Falls, WI (US)

(73) Assignee: Quest Technologies, Oconomowoc, WI (US)

( * ) Notice: Subject to any disclaimer, the term of this patent is extended or adjusted under 35 U.S.C. 154(b) by 0 days.

(21) Appl. No.: 11/846,131

(22) Filed: Aug. 28, 2007

(65) Prior Publication Data

US 2009/0056417 A1    Mar. 5, 2009

(51) Int. Cl.
*G01N 1/16* (2006.01)

(52) U.S. Cl. .................................. 73/863.33

(58) Field of Classification Search ............ None
See application file for complete search history.

(56) References Cited

U.S. PATENT DOCUMENTS

| | | | |
|---|---|---|---|
| 3,518,815 A | 7/1970 | McFarland et al. |
| 4,133,202 A | 1/1979 | Marple |
| 4,764,186 A | 8/1988 | Langer |
| 4,827,779 A | 5/1989 | Marple et al. |
| 4,906,094 A | 3/1990 | Ashida |
| 4,942,297 A | 7/1990 | Johnson et al. |
| 4,942,305 A | 7/1990 | Sommer |
| 5,024,526 A | 6/1991 | Von Redwitz |
| 5,043,591 A | 8/1991 | Ludlow et al. |
| 5,089,714 A | 2/1992 | Ludlow et al. |
| 5,090,233 A * | 2/1992 | Kogure et al. ............ 73/28.05 |
| 5,231,378 A | 7/1993 | Dennis et al. |
| 5,553,507 A | 9/1996 | Basch et al. |
| 5,702,506 A | 12/1997 | Shih et al. |
| 5,742,516 A | 4/1998 | Olcerst |
| 5,764,840 A | 6/1998 | Wach |
| 5,831,182 A | 11/1998 | Swenson |
| 5,932,795 A | 8/1999 | Koutrakis et al. |
| 5,983,732 A | 11/1999 | Hering et al. |
| 6,217,636 B1 * | 4/2001 | McFarland ................ 95/216 |

(Continued)

FOREIGN PATENT DOCUMENTS

DE    4339379 A1    5/1995

(Continued)

OTHER PUBLICATIONS

Quest Technologies, Indoor Air Quality Monitors, product brochure, Jun. 2002, 10 pages.

(Continued)

*Primary Examiner*—Robert R Raevis
(74) *Attorney, Agent, or Firm*—Anna A. Wetzels (57) ABSTRACT

A particulate monitor includes a housing, an air-moving device coupled to the housing, and an air passageway disposed at least partially within the housing. The air-moving device is operable to create an airflow through the air passageway. The particulate monitor also includes a real-time measuring device positioned at least partially within the housing and in fluid communication with the air passageway and a particulate collection device positioned at least partially within the housing and in fluid communication with the air passageway. The collection device is positioned downstream of the real-time measuring device.

21 Claims, 10 Drawing Sheets

U.S. PATENT DOCUMENTS

| | | | |
|---|---|---|---|
| 6,298,178 B1 | 10/2001 | Day et al. | |
| 6,342,388 B1 | 1/2002 | Van Den Wildenberg | |
| 6,414,754 B1 | 7/2002 | Johnson | |
| 6,442,998 B2 | 9/2002 | Kurokawa et al. | |
| 6,497,490 B1 | 12/2002 | Miller et al. | |
| 6,692,553 B2 * | 2/2004 | Jordan et al. | 95/285 |
| 6,723,568 B1 | 4/2004 | Liu et al. | |
| 6,829,919 B2 * | 12/2004 | Sioutas et al. | 73/28.04 |
| 6,964,190 B2 | 11/2005 | Shinohara et al. | |
| 7,073,402 B2 * | 7/2006 | Trakumas et al. | 73/863.22 |
| 7,135,060 B2 | 11/2006 | Jordan, Sr. et al. | |
| 7,155,988 B2 | 1/2007 | Cole et al. | |
| 7,173,257 B1 | 2/2007 | Warrick et al. | |
| 7,173,270 B1 | 2/2007 | Bruinsma et al. | |
| 7,197,911 B1 | 4/2007 | Lilienfeld | |
| 7,243,560 B2 | 7/2007 | Coyle et al. | |
| 2001/0029793 A1 | 10/2001 | Moler et al. | |
| 2003/0174317 A1 | 9/2003 | Murdock et al. | |
| 2004/0017568 A1 | 1/2004 | Wyatt | |
| 2004/0080747 A1 | 4/2004 | Cerni et al. | |
| 2005/0068528 A1 | 3/2005 | Altobelli et al. | |
| 2005/0160839 A1 * | 7/2005 | Rogers et al. | 73/863.31 |
| 2005/0178675 A1 | 8/2005 | Hall | |
| 2005/0179904 A1 | 8/2005 | Larsen et al. | |
| 2007/0256566 A1 * | 11/2007 | Faber et al. | 96/417 |

FOREIGN PATENT DOCUMENTS

| | | |
|---|---|---|
| DE | 10161914 | 9/2003 |
| JP | 56160744 | 12/1981 |
| JP | 8261930 | 10/1996 |
| JP | 2006208254 | 8/2006 |
| WO | WO 02/31469 A1 | 4/2002 |
| WO | 03002981 | 1/2003 |
| WO | WO 2007/009119 A2 | 1/2007 |
| WO | WO 2007/113567 | 10/2007 |

OTHER PUBLICATIONS

TSI, Inc., AeroTrak 9000 Nanoparticle Aerosol Monitor, product brochure, 2006, 4 pages.

TSI, Inc., Indoor Air Quality Instruments, product brochure, 2007, 4 pages.

Marple et al., *Aerodynamic Particle Size Calibration Of Optical Particle Counters*, J. Aerosol Sci., 1976, vol. 7, pp. 425 to 433.

Norton et al., *Development of Long-Lifetime, Low-Contamination Beam Dumps for NIF*, Lawrence Livermore National Laboratory, Dec. 9, 1996.

* cited by examiner

PARTICULATE MONITOR

FIELD OF THE INVENTION

The present invention relates to particulate monitors, and more particularly to indoor air quality monitors

BACKGROUND OF THE INVENTION

Some conventional indoor air quality ("IAQ") monitors typically include a housing, a filter cassette or cartridge within the housing, a pump operable to draw an airflow through the filter cartridge, and a single impactor positioned adjacent an inlet to an air passageway in the housing upstream of the filter cartridge. Impactors are typically configured to trap or filter particulates having a particular nominal size or greater (e.g., 10 microns or greater) to substantially prevent such particles from entering the air passageway and being collected in the filter cartridge. The single impactor is typically removable from the housing and can be replaced with another single impactor of a different size to trap or filter different-size particulates. Other conventional IAQ monitors include a real-time measuring system (e.g., an optical engine), rather than the filter cartridge, to immediately display the results of an indoor air quality test.

SUMMARY OF THE INVENTION

By changing out individual single impactors in typical IAQ monitors, one may collect samples comprised of different ranges of nominal sizes of particulates (e.g., samples of particulates having a nominal size of 10 microns or smaller, samples of particulates having a nominal size of 2.5 microns or smaller, etc.). With this information, one can isolate specific health concerns that might be caused by a particularly high concentration of particulates within a particular range of nominal sizes. However, changing out individual single impactors in preparation for sample collection in typical IAQ monitors can be cumbersome and time consuming.

The present invention provides, in one aspect, a particulate monitor including a housing, an air-moving device coupled to the housing, and an air passageway disposed at least partially within the housing. The air-moving device is operable to create an airflow through the air passageway. The particulate monitor also includes a real-time measuring device positioned at least partially within the housing and in fluid communication with the air passageway and a particulate collection device positioned at least partially within the housing and in fluid communication with the air passageway. The collection device is positioned downstream of the real-time measuring device.

The present invention provides, in another aspect, a particulate monitor including a housing, an air-moving device coupled to the housing, and a first air passageway disposed at least partially within the housing. The air-moving device is operable to create an airflow through the first air passageway. The particulate monitor also includes a first impactor coupled to the housing and a second air passageway at least partially containing therein the first impactor. The second air passageway is selectively fluidly communicable with the first air passageway. The particulate monitor further includes a second impactor coupled to the housing and a third air passageway at least partially containing therein the second impactor. The third air passageway is isolated from the second air passageway and selectively fluidly communicable with the first air passageway.

The present invention provides, in yet another aspect, a particulate monitor including a housing, an air-moving device coupled to the housing, and an air passageway disposed at least partially within the housing. The air-moving device is operable to create an airflow through the air passageway. The particulate monitor also includes at least one impactor movably coupled to the housing to be movable between a first position adjacent an inlet to the air passageway and a second position displaced from the inlet of the air passageway.

Other features and aspects of the invention will become apparent by consideration of the following detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

DETAILED DESCRIPTION

Figure 1:
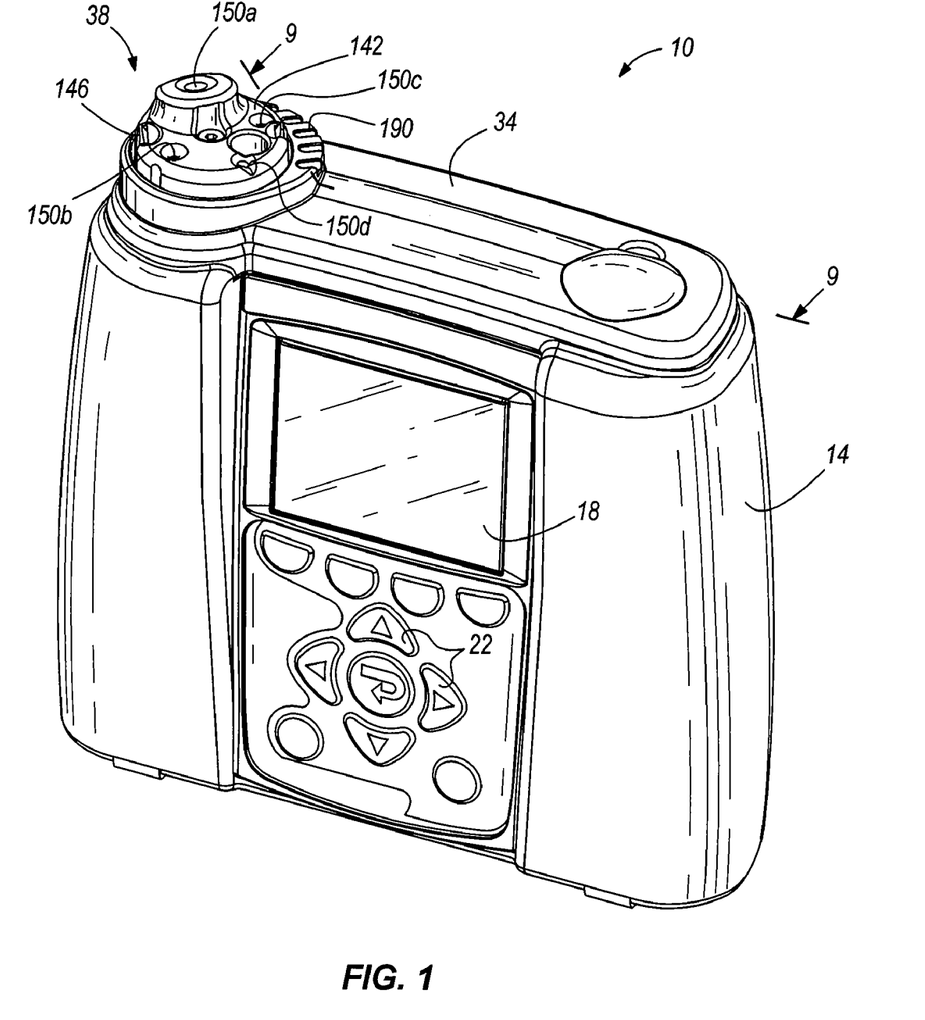
FIG. 1 is a front perspective view of a particulate monitor of the present invention.
Figure 2:
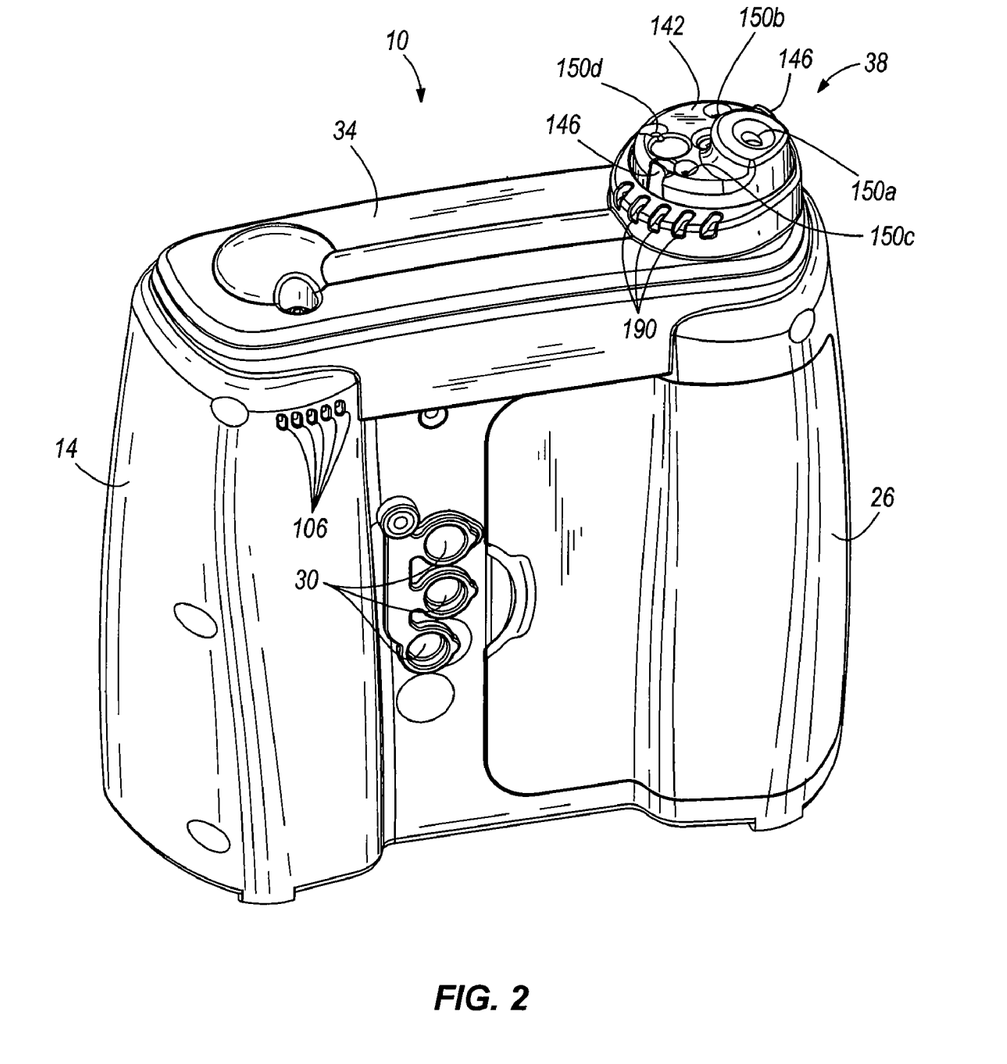
FIG. 2 is a rear perspective view of the particulate monitor of FIG. 1.

FIGS. 1 and 2 illustrate a particulate monitor or an IAQ monitor 10 utilized to collect data on the quantity and sizes of airborne particulates in a particular working space or environment to determine indoor air quality. The monitor 10 includes a housing 14, a display screen 18 on the front of the housing 14, and a plurality of user-manipulated controls 22 on the front of the housing 14 below the display screen 18 (see FIG. 1). With reference to FIG. 2, the monitor 10 also includes an access panel 26 removably coupled to the housing 14 for access to the interior of the housing 14. In the illustrated construction of the monitor 10, the access panel 26 incorporates a resiliently-deformable connector (e.g., a resilient tab, not shown) to engage a corresponding flat or edge on the housing 14. Alternatively, the access panel 26 may be secured to the housing 14 by conventional fasteners, hinges, or the like. The monitor 10 also includes a plurality of rubber or plastic plugs 30, each configured to prevent access to an electrical connector (e.g., a power inlet, a data transfer outlet, etc.) positioned behind the plug 30.

Figure 5:
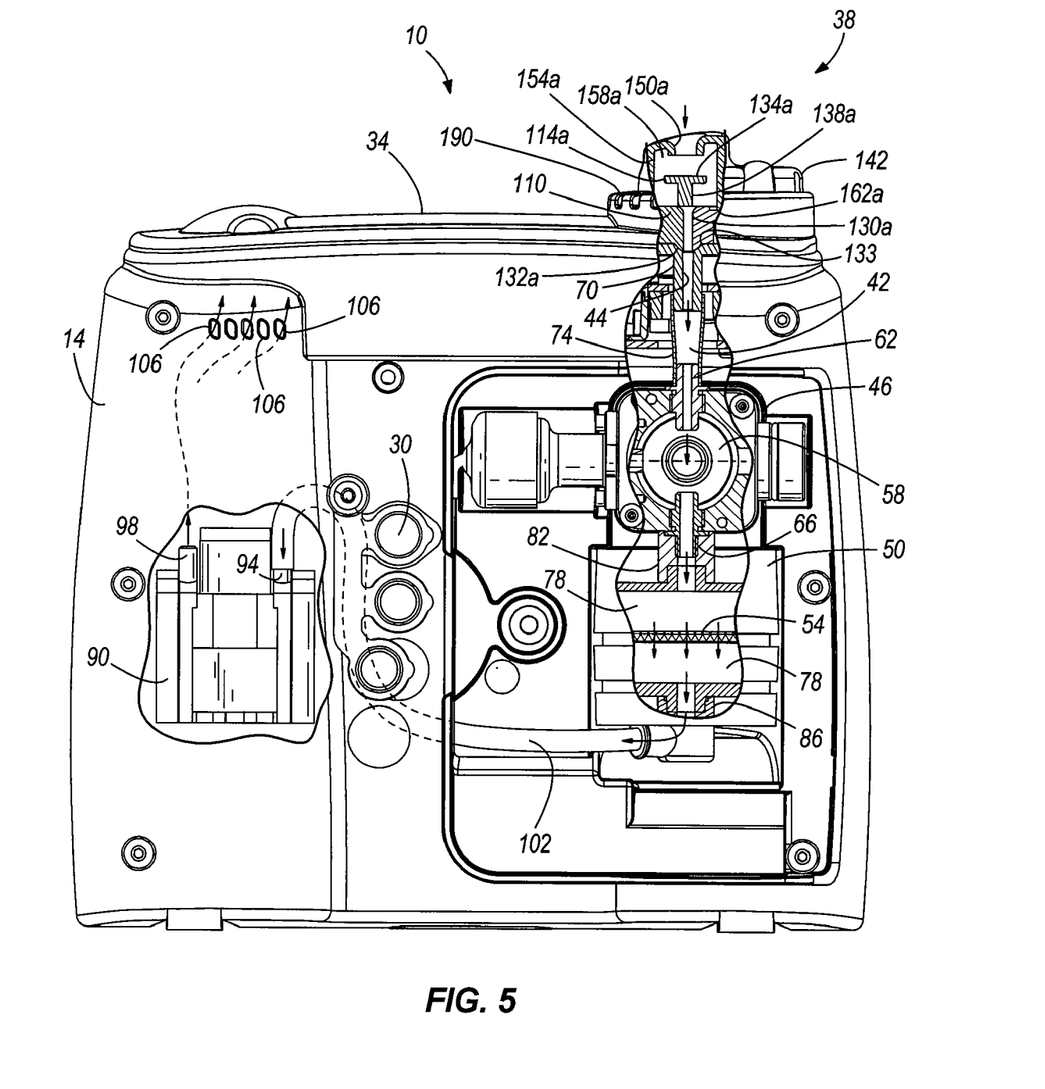
FIG. 5 is a rear, partial cutaway view of the particulate monitor of FIG. 1, illustrating the cap and turret rotated to a first position.

With reference to FIG. 1, the monitor 10 also includes a cover 34 coupled to the housing 14, and a rotatable impactor assembly 38 protruding from the cover 34. The monitor 10 includes an air passageway 42 within the housing 14, the inlet 44 of which is exposed to the bottom of the cover 34 beneath the rotatable impactor assembly 38 (see FIG. 5). With reference to FIG. 5, the monitor 10 includes a real-time measuring device 46 in the form of an optical engine 46 in fluid communication with the air passageway 42. As will be discussed in greater detail below, the optical engine 46 projects a laser through the air passageway 42 to collect data on the quantity and sizes of particulate matter entrained in an airflow passing through the passageway 42. Such an optical engine 46 is manufactured by Quest Technologies, Inc of Oconomowoc, Wis.

With continued reference to FIG. 5, the monitor 10 also includes a particulate collection device 50 positioned downstream of the measuring device 46 and in fluid communication with the air passageway 42. In the illustrated construction of the monitor 10, the particulate collection device 50 is in the form of a cylindrical, gravimetric filter cartridge 50 having a filter element 54 disposed therein. As will be discussed in greater detail below, particulate matter is collected on the filter element 54 after being measured by the optical engine 46 for subsequent analysis in a laboratory. As such, the filter cartridge 50 is removable through the access panel 26. Such a filter cartridge 50 is manufactured by SKC, Inc of Eighty Four, Pa. or Millipore Corporation of Billerica, Mass., and are available in a number of different standard sizes (e.g., 25 mm, 37 mm, etc.). Further, in an alternative construction of the monitor 10, the filter cartridge 50 may be disposed at least partially outside of the housing 14 to facilitate removal of the filter cartridge 50 from the housing 14. In the illustrated construction of the monitor 10, and in the alternative constructions described above, no portion of the filter cartridge 50 is positioned upstream of the measuring device 46.

With continued reference to FIG. 5, the air passageway 42 is defined by multiple components within the housing 14. In the illustrated construction of the monitor 10, the air passageway 42 is partially defined by the interior space 58 of the optical engine 46 through which the entrained particulate matter passes with the airflow, and respective inlet and outlet conduits 62, 66 extending from an upper surface of the optical engine 46 and a lower surface of the optical engine 46. The air passageway 42 is also partially defined by a conduit 70 integrally formed with the cover 34 and another conduit 74 (e.g., a plastic tube or hose) coupling the conduit 70 and the inlet conduit 62 on the optical engine 46. In the illustrated construction of the monitor 10, the inlet 44 of the air passageway 42 coincides with the inlet of the conduit 70.

The air passageway 42 is also partially defined by the interior space 78 of the filter cartridge 50 and respective inlet and outlet conduits 82, 86 extending from an upper surface of the filter cartridge 50 and a lower surface of the filter cartridge 50. In the illustrated construction of the monitor 10, the inlet conduit 82 on the filter cartridge 50 is sized to at least partially receive therein the outlet conduit 66 on the optical engine 46. Specifically, the inner diameter of the inlet conduit 82 and the outer diameter of the outlet conduit 66 are sized to allow the outlet conduit 66 of the optical engine 46 to be inserted within the inlet conduit 82 of the filter cartridge 50. As a result, the filter cartridge 50 may be removably coupled to the optical engine 46 by the slip-fit between the inlet conduit 82 of the filter cartridge 50 and the outlet conduit 66 of the optical engine 46.

With continued reference to FIG. 5, the monitor 10 further includes an air-moving device 90 operable to create an airflow through the air passageway 42. In the illustrated construction of the monitor 10, the air-moving device 90 is in the form of a diaphragm pump 90 having an inlet 94 and an outlet 98. Such a pump 90 is manufactured by UNO International, Ltd. of London, United Kingdom. A connecting conduit 102 (e.g., a plastic tube or hose) is utilized to fluidly communicate the air passageway 42 and the pump 90. The conduit 102 may be sized to provide a slip-fit between the connecting conduit 102 and the outlet conduit 86 of the filter cartridge 50 so that the connecting conduit 102 may be removably coupled to the filter cartridge 50. The housing 14 includes a plurality of outlet openings 106 formed therein to fluidly communicate the interior of the housing 14 with the outside environment of the monitor 10. As will be explained in greater detail below, the airflow discharged by the pump 90 into the interior of the housing 14 may be exhausted through the outlet openings 106 in the housing 14.

Figure 3:
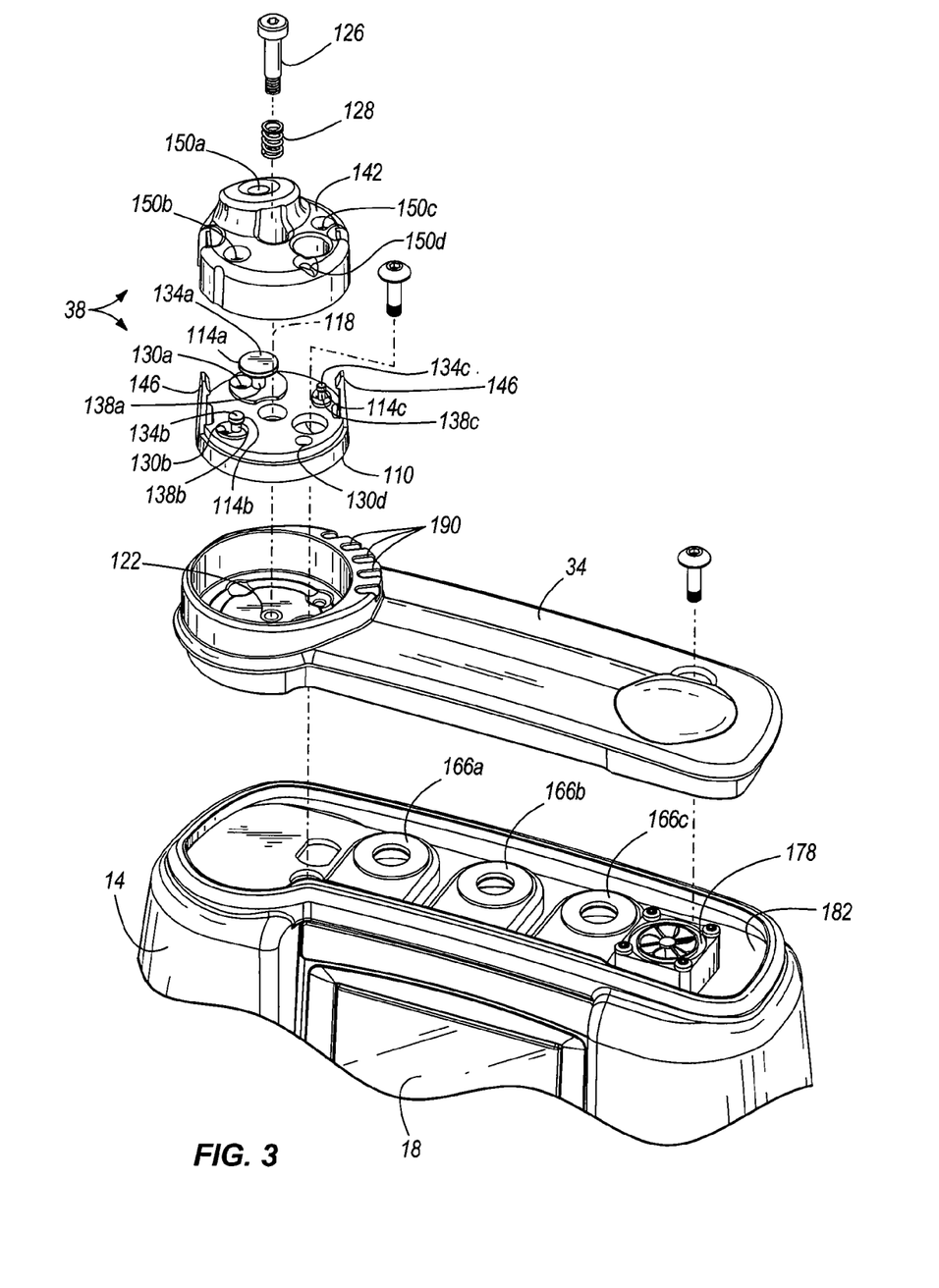
FIG. 3 is an enlarged, exploded top perspective view of a portion of the particulate monitor of FIG. 1, illustrating a rotatable turret, a plurality of impactors coupled to the turret, and a cap coupled to the turret to at least partially cover the impactors.

With reference to FIG. 3, the components of the impactor assembly 38 are shown. In the illustrated construction of the monitor 10, the impactor assembly 38 includes a movable platform 110 in the form of a rotatable turret 110 supporting a plurality of impactors 114a, 114b, 114c thereon. The turret 110 is rotatable about a central axis 118 and is coupled to the cover 34 for rotation about the central axis 118. In the illustrated construction of the monitor 10, a threaded insert 122 is molded into the cover 34, and a fastener 126 is threaded into the insert 122 to secure the turret 110 to the cover 34 yet allow rotation of the turret 110 with respect to the cover 34 and housing 14. A compression spring 128 is positioned between the fastener 126 and the turret 110 to downwardly bias the turret 110. Alternatively, other structure may be utilized to rotatably couple the turret 110 to the cover 34 and housing 14. Further, in an alternative construction of the monitor 10, the movable platform 110 may be configured as an axially-slidable member, rather than the rotatable turret 110.

Figure 4A:
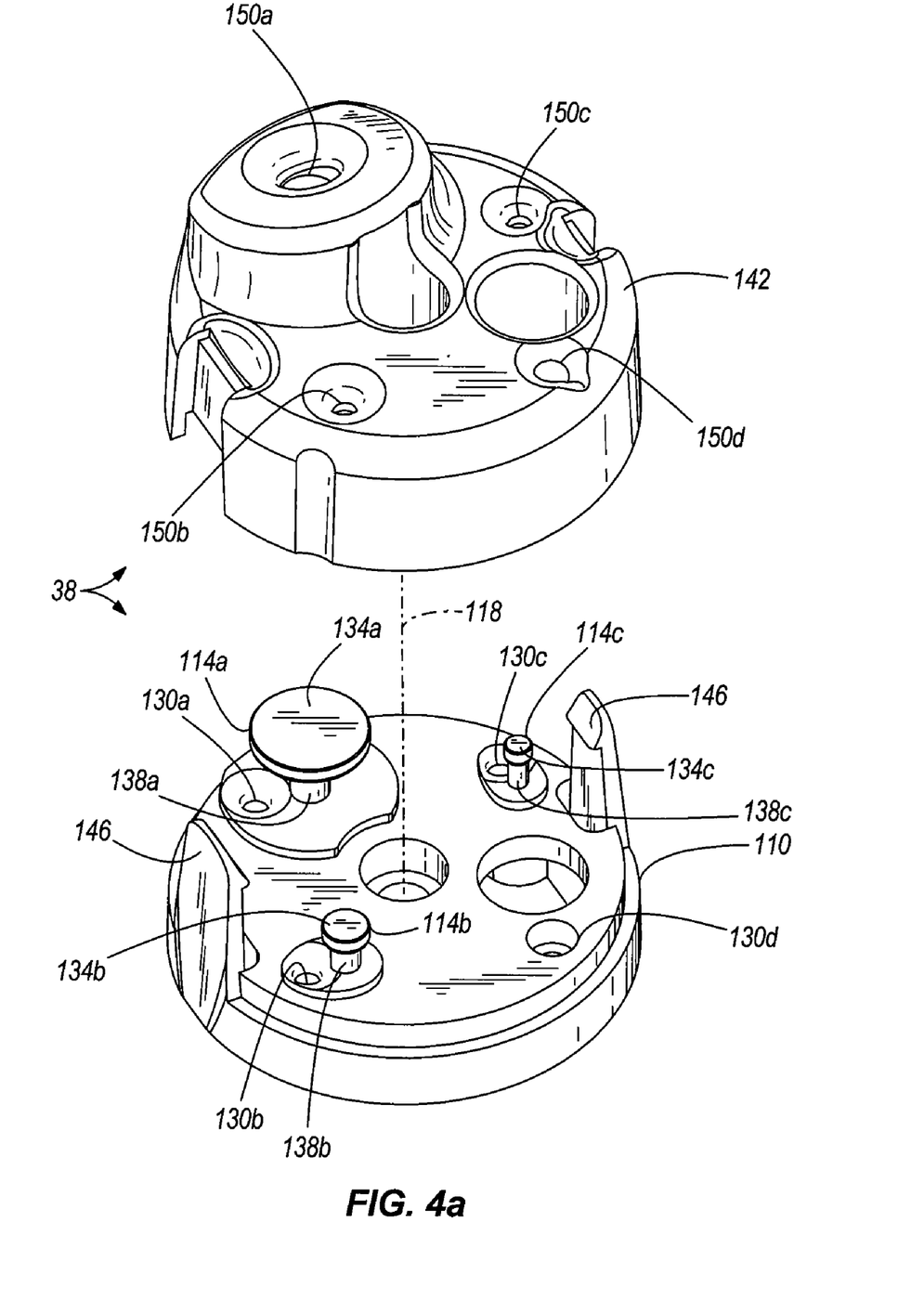
FIG. 4a is an enlarged, exploded top perspective view of the turret and cap shown in FIG. 3.
Figure 4B:
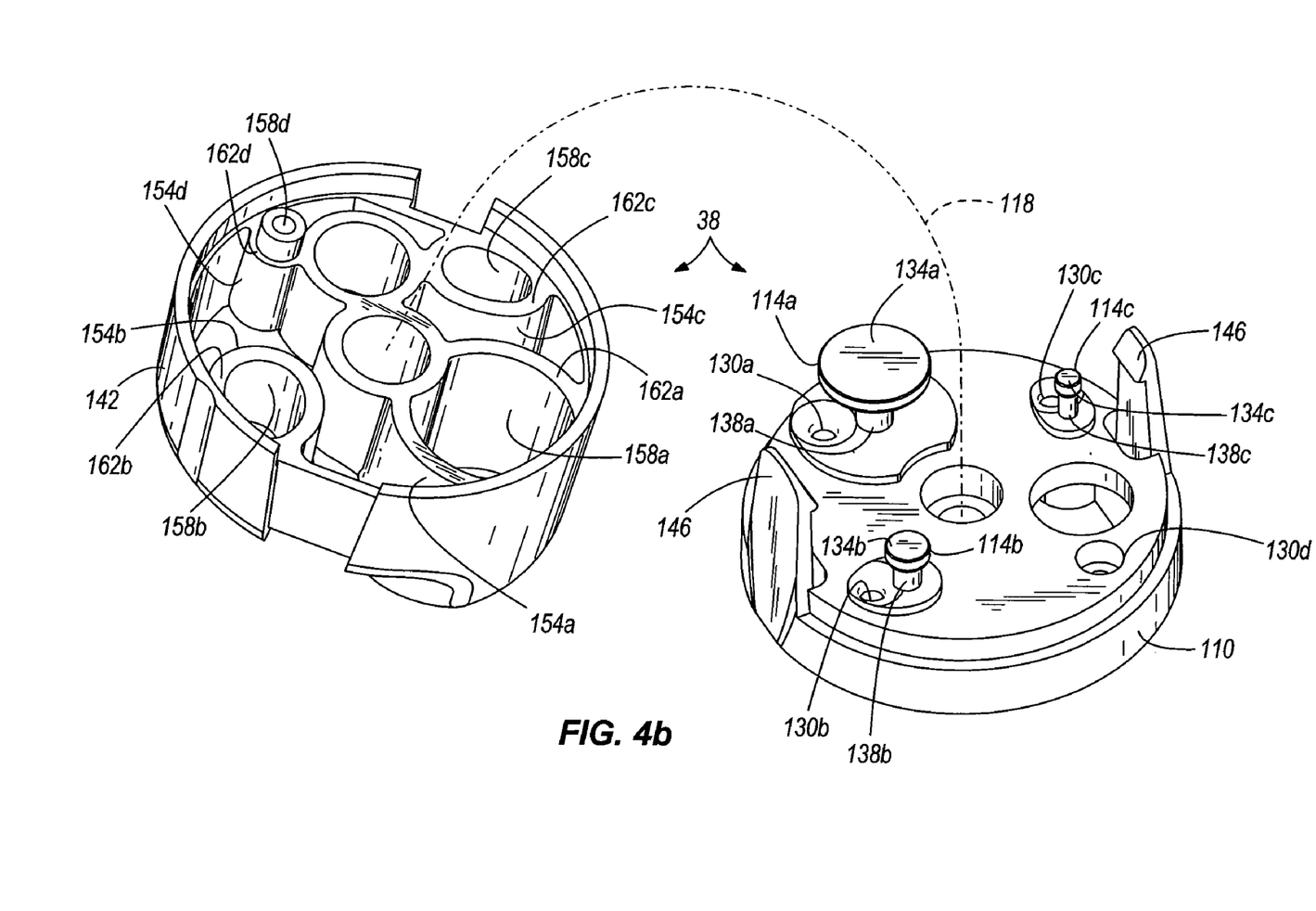
FIG. 4b is an enlarged, exploded top perspective view of the turret and a bottom perspective view of the cap shown in FIG. 3, illustrating the interior of the cap.

With reference to FIGS. 4a and 4b, the illustrated turret 110 includes four apertures 130a-130d therethrough, each spaced a substantially similar radial distance from the central axis 118, and each spaced an equi-angular distance (e.g., 90 degrees) from one-another. Particularly, the apertures 130a-130d are spaced from the central axis 118 by the same radial distance as the inlet 44 of the air passageway 42, such that any one of the apertures 130a-130d may be aligned with the inlet 44 of the air passageway 42 depending upon the rotational position of the turret 110. With reference to FIGS. 5-8, the bottom of the turret 110 includes respective raised surfaces 132a-132d surrounding the respective apertures 130a-130d that selectively engage a depression 133 in the cover 34 surrounding the inlet 44 of the air passageway 42. The spring 128 (see FIG. 3) biases the turret 110 toward the cover 34 such that the respective raised surfaces 132a-132d serve as locating features for the respective apertures 130a-130d in the turret 110. Of course, other locating features can also be used.

With reference to FIGS. 4a and 4b, the impactors 114a-114c are positioned adjacent the respective apertures 130a-130c in the turret 110, while the aperture 130d is not associated with an adjacent impactor. In the illustrated construction of the monitor 10, each of the impactors 114a-114c includes a respective platform 134a-134c and a pedestal 138a-138c supporting the platforms 134a-134c above the turret 110. Although the illustrated pedestals 138a-138c are substantially similar to one another, the respective platforms 134a-134c are differently sized to provide different levels of particulate matter filtration to the airflow entering the air passageway 42. For example, the impactor 114a may be sized to trap or filter particulate matter in the airflow leading to the air passageway 42 having a nominal size of 1 micron or greater, while the other impactors 114b, 114c may be sized to trap or filter particulate matter in the airflow leading to the air passageway 42 having a nominal size of 2.5 microns or greater, and 10 microns or greater, respectively. As such, the impactor 114c is more of a "coarse" filter than the impactor 114a. The filtration process is discussed in more detail below. Although the illustrated turret 110 incorporates only three impactors 114a-114c, an alternative construction of the monitor 10 may incorporate more or less than three impactors, each associated with a respective aperture in the turret 110. Alternatively, differently-sized impactors may be substituted for those shown (e.g., an impactor sized to trap or filter particulate matter in the airflow leading to the air passageway 42 having a nominal size of 4 microns or greater.)

With continued reference to FIGS. 4a and 4b, the rotatable impactor assembly 38 also includes a cap 142 coupled to the turret 110 to at least partially cover or enclose the impactors 114a-114c. In the illustrated construction of the monitor 10, resiliently-deformable connectors 146 are utilized to secure the cap 142 to the turret 110. Although the connectors 146 are shown extending from the turret 110, the connectors 146 may alternatively extend from the cap 142 to engage the turret 110. As a further alternative, the cap 142 may be coupled to the turret 110 using conventional fasteners or the like.

With reference to FIG. 4a, the cap 142 includes three apertures 150a-150c that, when the cap 142 is coupled to the turret 110, are substantially aligned with the respective impactors 114a-114c on the turret 110. As a result, the apertures 150a-150c in the cap 142 are offset from the apertures 130a-130c in the turret 110. The cap 142 includes an additional aperture 150d that is aligned with the aperture 130d in the turret 110 not associated with an adjacent impactor. With reference to FIG. 4b, the cap 142 includes four cylindrical walls or conduits 154a-154d, associated with the respective apertures 150a-150d in the cap 142, extending toward the turret 110. Each of the conduits 154a-154d defines a passageway 158a-158d therein to communicate airflow entering the respective passageways 158a-158d via the apertures 150a-150d to the air passageway 42.

Figure 8:
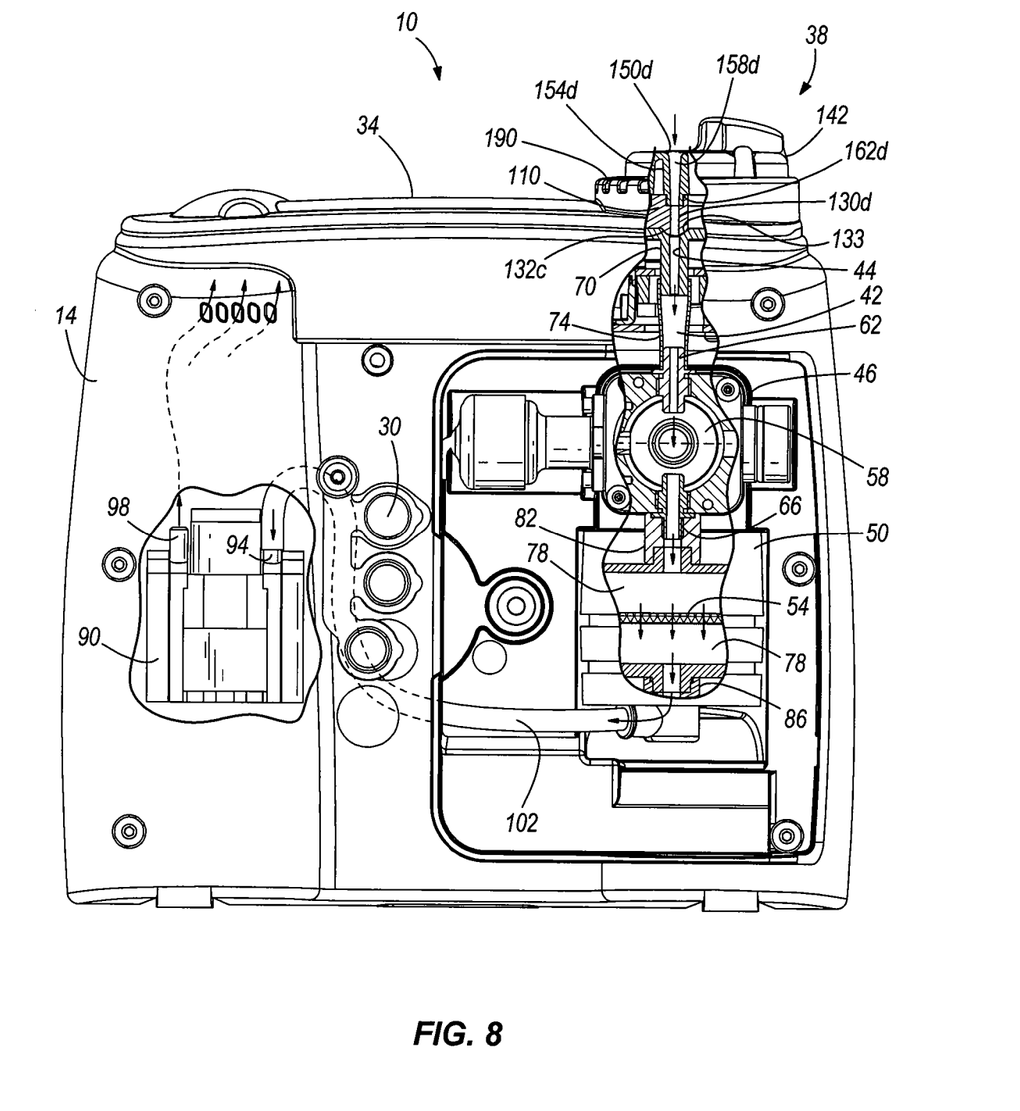
FIG. 8 is a rear, partial cutaway view of the particulate monitor of FIG. 1, illustrating the cap and turret rotated to a fourth position.

As shown in FIGS. 5-8, each of the conduits 154a-154d includes a lower end 162a-162d engaged with the turret 110, such that the passageways 158a-158d defined by the conduits 154a-154d are separated and isolated from one another. With reference to FIG. 5, the impactor 114a is contained within the passageway 158a in the cap 142, and the aperture 130a in the turret 110 provides an outlet for the passageway 158a. Likewise, the impactor 114b is contained within the passageway 158b in the cap 142, and the aperture 130b in the turret 110 provides an outlet for the passageway 158b (see FIG. 6). The impactor 114c is contained within the passageway 158c in the cap 142, and the aperture 130c provides an outlet for the passageway 158c (see FIG. 7). As shown in FIG. 8, the aperture 130d in the turret 110 provides an outlet for the passageway 158d.

Figure 9:
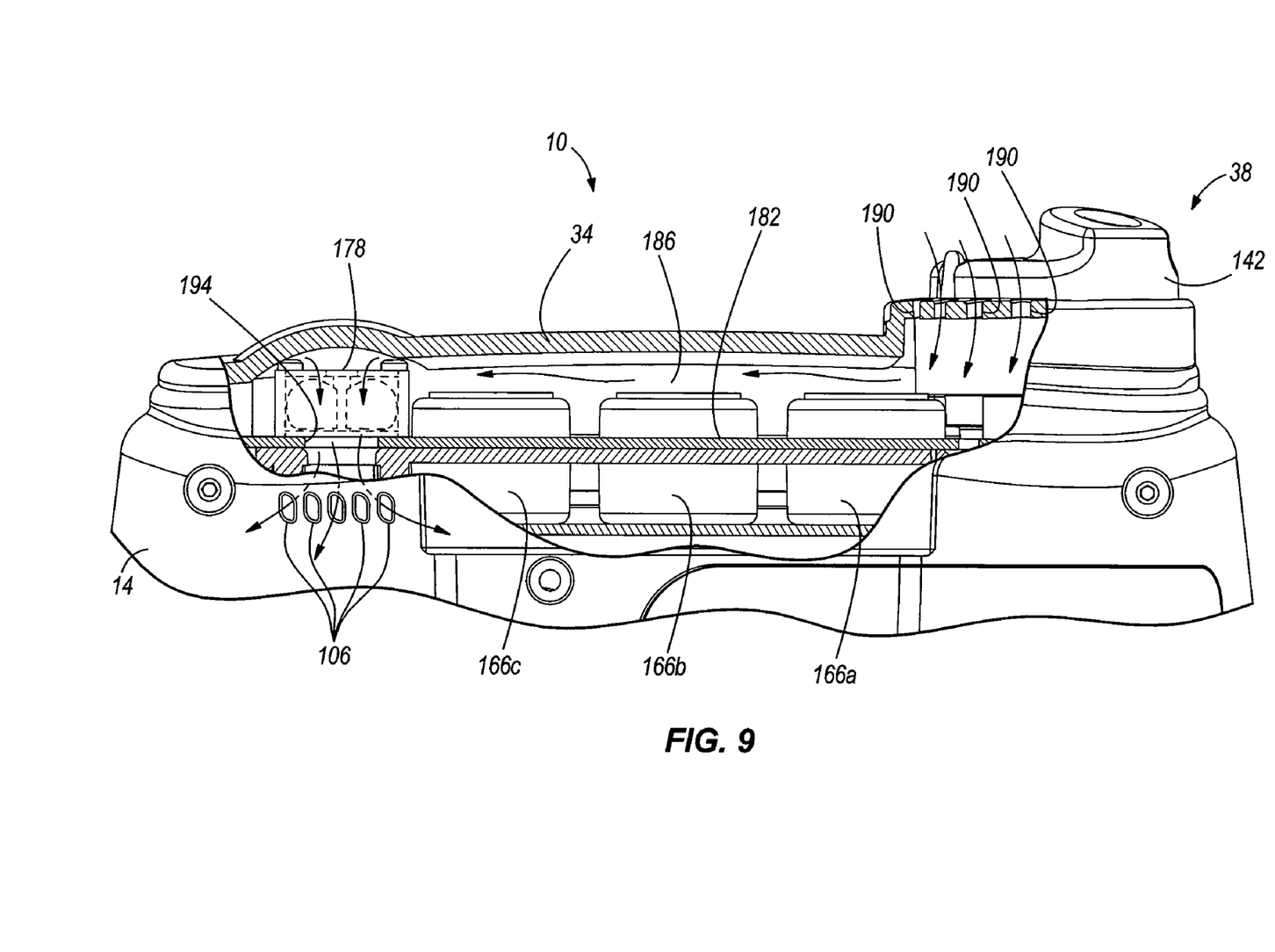
FIG. 9 is a partial cross-sectional view of the particulate monitor of FIG. 1 through line 9-9 in FIG. 1.

With reference to FIGS. 3 and 9, the monitor 10 includes other real-time measuring devices 166a-166c, in addition to the optical engine 46, coupled to the housing 14. In the illustrated construction of the monitor 10, the measuring devices 166a-166c include a carbon dioxide sensor 166a, a toxic gas (e.g., carbon monoxide, hydrogen sulfide, sulfur dioxide, nitrogen oxides, and nitrogen dioxide) sensor 166b, and a photoionization detector ("PID") 166c. The carbon dioxide sensor 166a is configured to detect by diffusion the amount of carbon dioxide present in an airflow over the sensor 166a. Such a sensor 166a is manufactured by City Technology Ltd. of Hampshire, United Kingdom. Likewise, the toxic gas sensor 166b is configured to detect by diffusion the amount of carbon monoxide or other toxic gases present in an airflow over the sensor 166b. Such a sensor 166b is manufactured by Dr. Alan Doncaster of Witham, United Kingdom. The PID 166c is configured to detect by diffusion the amount of volatile organic compounds ("VOCs", e.g., caulks, glues, etc.) present in an airflow over the PID 166c. Such a PID 166c is manufactured by Ion Science Ltd. of Cambridge, United Kingdom. Additionally, other sensors or detectors may be incorporated with the devices 166a-166c or separately (e.g., a temperature sensor, a humidity sensor, etc.). The illustrated monitor 10 also includes such temperature and humidity sensing capabilities.

With continued reference to FIG. 9, the monitor 10 includes an air-moving device 178 in the form of an axial-flow fan 178 coupled to the housing 14 and positioned adjacent the group of devices 166a-166c. Such an axial-flow fan 178 is manufactured by ADDA Corporation of Taiwan. Specifically, the fan 178 and devices 166a-166c are supported on a printed circuit board ("PCB") 182 coupled to the housing 14. The fan 178 is electrically connected to the PCB 182 to receive power therefrom, and the devices 166a-166c (an other sensors such as temperature and humidity sensors) are electrically connected to the PCB 182 to receive power therefrom and transmit the output of each of the devices 166a-166c to a microprocessor (not shown) in a conventional manner.

The cover 34 and the PCB 182 define therebetween an air passageway 186 separate and distinct from any of the other air passageways 42, 158a-158d in the monitor 10. As shown in FIGS. 1-3 and FIG. 9, the cover 34 includes a plurality of inlet openings 190 adjacent the impactor assembly 38 to allow an airflow to enter the passageway 186. The PCB 182 includes a cutout 194 beneath the fan 178 to allow the fan 178 to discharge the airflow in the passageway 186 into the interior of the monitor housing 14. As will be discussed in greater detail below, the airflow discharged by the axial fan 178 into the interior of the housing 14 via the cutout 194 in the PCB 182 may be exhausted through the outlet openings 106 in the housing 14 (see FIG. 9).

Before using the monitor 10, the cap 142 is removed from the turret 110 to apply an adhesive or gel substance (e.g., petroleum jelly) on the respective platforms 134a-134c of the impactors 114a-114c, in a conventional manner, to catch or trap particulate matter of a desired nominal size or greater before entering the air passageway 42 for measurement by the optical engine 46 and subsequent collection by the filter cartridge 50. After the adhesive or gel substance is applied to all of the impactors 114a-114c, the cap 142 may be replaced onto the turret 110, and the impactor assembly 38 may be moved (e.g., rotated) to align the respective aperture 130a-130c associated with the intended impactor 114a-114c to be used with the inlet 44 of the air passageway 42.

Operation of the monitor 10 is described below with reference to FIG. 5, which illustrates the impactor assembly 38 "dialed" to the position of impactor 114a. However, operation of the monitor 10 is substantially similar when the impactor assembly 38 is dialed to the position of any of the other impactors 114b, 114c. During an IAQ test, the pump 90 is operated to draw a continuous airflow through the air passageway 42, through the aperture 130a in the turret 110 aligned with the inlet 44 of the air passageway 42, through the passageway 158a in the cap 142, and through the aperture 150a in the cap 142. Because the aperture 150a in the cap 142 is positioned over and aligned with the impactor 114a, the impactor 114a redirects the airflow as it moves through the passageway 158a in the cap 142. Particulate matter entrained in the airflow, particularly heavier and larger particulates, tend to respond less to the redirection of the airflow than lighter and smaller particulates, making it more likely that heavier and larger particulates impinge upon the platform 134a and become trapped in the adhesive or gel substance on the platform 134a. As a result, particulate matter having a nominal size of 1 micron or less is likely to be redirected with the airflow around the impactor 114a in the passageway 158a in the cap 142. The airflow (containing particulate matter having a nominal size of 1 micron or less) then flows through the aperture 130a in the turret 110 and enters the air passageway 42 via the inlet 44.

With reference to FIG. 8, The impactor assembly 38 is shown "dialed" to the position in which the aperture 130d in the turret 110 is aligned with the inlet 44 of the air passageway 42. Because no impactor is contained within the passageway 158d in the cap 142, no particulate matter is trapped or filtered before the airflow enters the air passageway 42. As a result, particulate matter of varying sizes is measured by the optical engine 46 and collected by the filter cartridge 50.

With reference back to FIG. 5, upon entering the air passageway 42, the airflow passes through the optical engine 46 for real-time measurement of the amount and sizes of the entrained particulate matter, and immediately thereafter is passed through the filter cartridge 50 to collect samples of the particulate matter that was measured by the optical engine 46. During the IAQ test, the results of the measurement by the optical engine 46 are displayed in real time on the display screen 18 (see FIG. 1) and/or can be output from the monitor 10 via a data transfer outlet located behind one or more of the plugs 30. After completion of the IAQ test, the filter cartridge 50 may be removed from the housing 14 as described above to send to a laboratory to perform additional or supplemental testing or analysis of the collected particulate matter. Alternatively, the monitor 10 may be operated during an IAQ test using only the optical engine 46 to view in real time the results of the measurements taken by the optical engine 46. In such a manner of operation, the filter element 54 may be omitted from the filter cartridge 50, thereby providing a "blank" cartridge. In the illustrated embodiment, a blank cartridge may be utilized to complete the air passageway 42 without collecting or filtering particulate matter from the airflow. In other embodiments, the air passageway 42 could be re-configured so that the filter cartridge 50 could be removed without being replaced with a blank cartridge. Also, the monitor 10 may alternatively be operated during an IAQ test using only the filter cartridge 50 to collect particulate matter samples, without first measuring the particles using the optical engine 46. In such a manner of operation, the optical engine 46 may be deactivated.

While the pump 90 and optical engine 46 are functioning, the monitor 10 is operable to perform additional air quality testing using the sensors 166a, 166b and the PID 166c. Specifically, the axial fan 178 may be energized to draw an airflow through the inlet openings 190 in the cover 34, and through the passageway 186 between the cover 34 and the PCB 182 and over the sensors 166a, 166b and the PID 166c. As the airflow passes over the sensors 166a, 166b, the sensors 166a, 166b detect the amount of carbon dioxide and toxic gases (e.g., carbon monoxide, etc.), respectively, present in the airflow and output the results of the measurements to the PCB 182 and ultimately to the display screen 18 for real-time observation. As the airflow passes over the PID 166c, it detects the amount of VOCs present in the airflow and outputs the results of the measurement to the PCB 182 and ultimately to the display screen 18 and/or data transfer outlet) for real-time observation.

The axial fan 178 may then discharge the airflow through the cutout 194 in the PCB 182 and into the interior of the housing 14 where it may combine with the filtered airflow exiting the outlet 98 of the pump 90. The combined airflow may then exit the interior of the housing 14 via the outlet openings 106 in the housing 14.

After completion of an IAQ test, the impactor turret 110 may be moved (e.g., rotated) or dialed without the use of tools to the position in which the aperture 130b in the turret 110 is aligned with the inlet 44 of the air passageway 42 (see FIG. 6) to utilize the impactor 114b. To rotate the turret 110, one could grasp the cap 142 and apply an amount of torque to the cap 142 sufficient to cause the raised surface 132a to disengage the depression 133 and displace the turret 110 and cap 142 upwardly against the bias of the spring 128, allowing the cap 142 and turret 110 to be rotated in a counter-clockwise direction until the raised surface 132b falls into the depression 133 to indicate to the user that the impactor 114b is ready to be used. Further, the filter cartridge 50 may be replaced with a fresh cartridge 50, and another IAQ test may be immediately performed without the substantial downtime associated with removing an impactor and replacing it with another as required in some conventional IAQ monitors.

Figure 6:
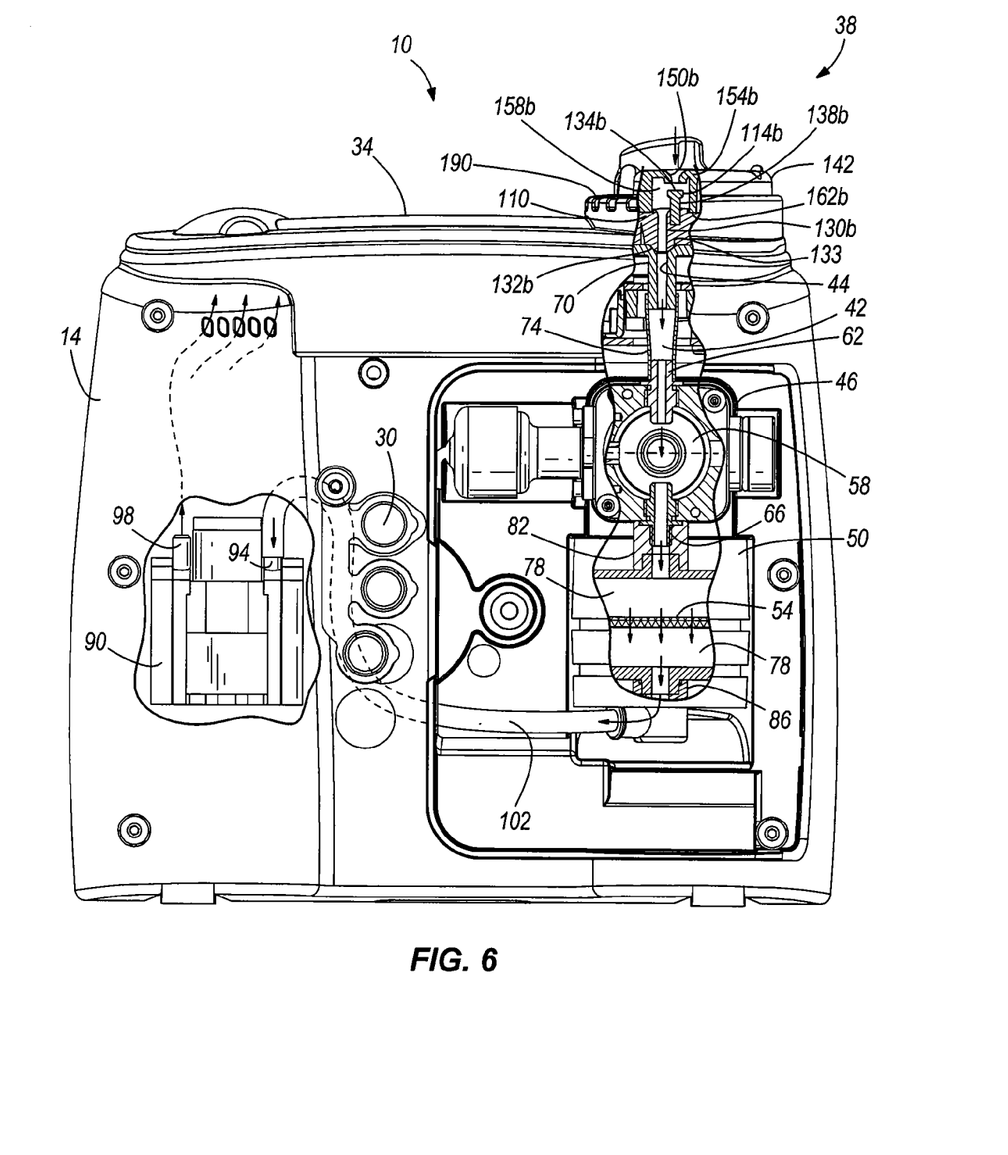
FIG. 6 is a rear, partial cutaway view of the particulate monitor of FIG. 1, illustrating the cap and turret rotated to a second position.
Figure 7:
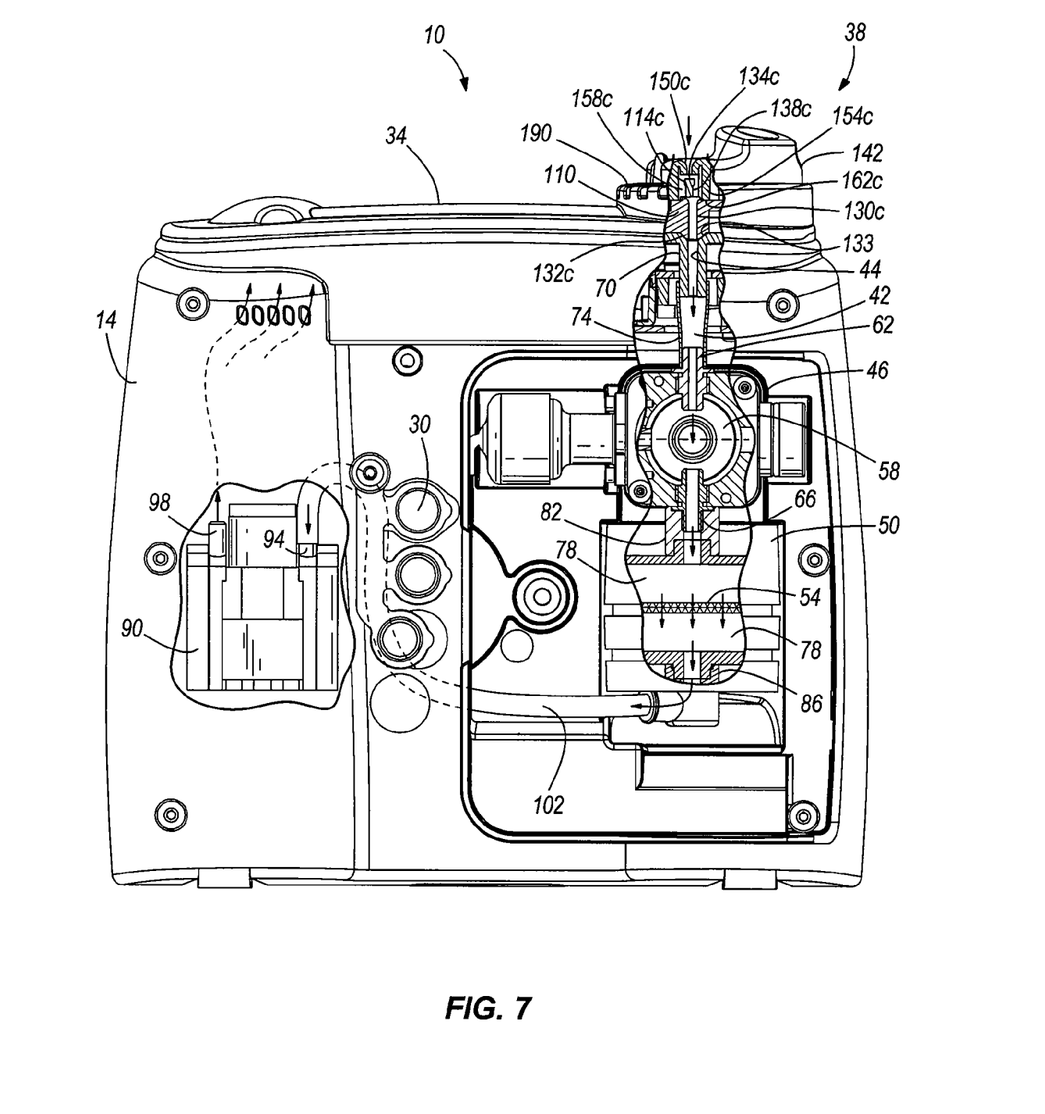
FIG. 7 is a rear, partial cutaway view of the particulate monitor of FIG. 1, illustrating the cap and turret rotated to a third position.

After completion of the IAQ test using the impactor 114b shown in FIG. 6, the turret 110 may be rotated or dialed to the position in which the aperture 130c in the turret 110 is aligned with the inlet 44 of the air passageway 42 (see FIG. 7) to utilize the impactor 114c, the filter cartridge 50 may be replaced with a fresh cartridge 50, and another IAQ test may be immediately performed. Additional IAQ testing may be performed in the same manner by dialing the turret 110 to the position associated with the aperture 130d in the turret 110 that is not associated with an impactor (see FIG. 8).

As shown in FIGS. 1 and 2, the monitor 10 is compact and portable so to be carried by a user while conducting IAQ tests. Because the monitor 10 is portable, IAQ testing may be easily performed by a user in different locations or areas of a particular testing environment, without connecting the monitor 10 to bulky, substantially non-portable data acquisition equipment.

Various features of the invention are set forth in the following claims.

What is claimed is:

1. A particulate monitor comprising:
   a housing;
   an air-moving device coupled to the housing;
   a first air passageway disposed at least partially within the housing, the air moving device operable to create an airflow through the air passageway;
   a first impactor coupled to the housing;

a second air passageway at least partially containing therein the first impactor;
a second impactor coupled to the housing; and
a third air passageway at least partially containing therein the second impactor, the third air passageway isolated from the second air passageway;
wherein the first air passageway is selectively fluidly communicable with no more than one of the second air passageway or the third air passageway.

2. The particulate monitor of claim 1, further comprising:
a particulate collection device positioned at least partially within the housing and in fluid communication with the first air passageway.

3. The particulate monitor of claim 1, further comprising an optical engine positioned at least partially within the housing configured to project light through the first passageway.

4. The particulate monitor of claim 1, further comprising:
a third impactor coupled to the housing; and
a fourth air passageway at least partially containing therein the third impactor, the fourth air passageway isolated from the second air passageway and the third air passageway;
wherein the first air passageway is selectively fluidly communicable with no more than one of the second air passageway, the third air passageway, or the fourth air passageway.

5. The particulate monitor of claim 1, further comprising a fourth air passageway isolated from the second air passageway and the third air passageway;
wherein the first air passage way is selectively fluidly communicable with no more than one of the second air passageway, the third air passageway, or the fourth air passageway.

6. The particulate monitor of claim 1, wherein each of the first impactor and the second impactor is movably coupled to the housing to be movable between a first position adjacent an inlet to the first air passageway and a second position displaced from the inlet of the first air passageway.

7. The particulate monitor of claim 6, wherein each of the first impactor and the second impactor is movable between the first position and the second position without using tools.

8. The particulate monitor of claim 6, further comprising a platform movably coupled to the housing, wherein at least one of the first impactor and the second impactor is supported on the platform.

9. A particulate monitor comprising:
a housing;
an air-moving device coupled to the housing;
a first air passageway disposed at least partially within the housing, the air moving device operable to create an airflow through the air passageway;
a first impactor coupled to the housing;
a second air passageway at least partially containing therein the first impactor, the second air passageway selectively fluidly communicable with the first air passageway;
a second impactor coupled to the housing;
a third air passageway at least partially containing therein the second impactor, the third air passageway isolated from the second air passageway and selectively fluidly communicable with the first air passageway; and
a platform movably coupled to the housing,
wherein both of the first impactor and the second impactor are supported on the platform;
wherein the platform includes a first aperture that selectively fluidly communicates the first air passageway with the second air passageway, and wherein the platform includes a second aperture that selectively fluidly communicates the first air passageway with the third air passageway; and
wherein each of the first impactor and the second impactor is movable between a first position adjacent an inlet to the first air passageway and a second position displaced from the inlet of the first air passageway.

10. The particulate monitor of claim 9, further comprising:
a particulate collection device positioned at least partially within the housing and in fluid communication with the first air passageway.

11. The particulate monitor of claim 9, further comprising an optical engine positioned at least partially within the housing configured to project light through the first passageway.

12. The particulate monitor of claim 9, wherein the platform at least partially defines a turret rotatably coupled to the housing.

13. The particulate monitor of claim 9, further comprising a cap coupled to the platform to at least partially cover the first impactor and the second impactor, wherein the second air passageway is at least partially defined by the cap, and wherein the third air passageway is at least partially defined by the cap.

14. The particulate monitor of claim 13, wherein the cap includes a first aperture substantially aligned with the first impactor and a second aperture substantially aligned with the second impactor, wherein an airflow may enter the second passageway via the first aperture in the cap, and wherein an airflow may enter the third passageway via the second aperture in the cap.

15. The particulate monitor of claim 9, wherein the platform is removable from the housing.

16. A particulate monitor comprising:
a housing;
an air-moving device coupled to the housing;
a first air passageway disposed at least partially within the housing, the air moving device operable to create an airflow through the air passageway;
a first impactor coupled to the housing;
a second air passageway at least partially containing therein the first impactor, the second air passageway selectively fluidly communicable with the first air passageway;
a second impactor coupled to the housing; and
a third air passageway at least partially containing therein the second impactor, the third air passageway isolated from the second air passageway and selectively fluidly communicable with the first air passageway;
and further comprising:
a real-time measuring device positioned at least partially within the housing and in fluid communication with the first air passageway; and
a particulate collection device positioned at least partially within the housing and in fluid communication with the first air passageway, the collection device positioned downstream of the real-time measuring device.

17. The particulate monitor of claim 16, wherein the real-time measuring device includes an optical engine.

18. The particulate monitor of claim 16, wherein the particulate collection device includes a filter cartridge having a filter element therein.

19. The particulate monitor of claim 16, wherein the air moving device is a first air moving device, wherein the real-time measuring device is a first real-time measuring device, and wherein the particulate monitor further comprises:
a second air-moving device coupled to the housing;

a fourth air passageway disposed at least partially within the housing, the second air-moving device operable to create an airflow through the fourth air passageway; and a second real-time measuring device disposed at least partially within the fourth air passageway.

20. The particulate monitor of claim 19, wherein the second real-time measuring device includes at least one of a carbon dioxide sensor, a carbon monoxide sensor, and a photoionization detector.

21. The particulate monitor of claim 19, wherein the second air-moving device includes a fan.

* * * * *